United States Patent
Murphy et al.

(10) Patent No.: US 9,839,791 B2
(45) Date of Patent: Dec. 12, 2017

(54) APPARATUS AND METHOD FOR INHIBITING MELATONIN SYNTHESIS IN A HORSE

(75) Inventors: Barbara Murphy, Sallins (IE); John Sheridan, Dublin (IE)

(73) Assignee: EQUILUME LIMITED, Kildare (IE)

( * ) Notice: Subject to any disclaimer, the term of this patent is extended or adjusted under 35 U.S.C. 154(b) by 702 days.

(21) Appl. No.: 14/118,783

(22) PCT Filed: May 24, 2012

(86) PCT No.: PCT/EP2012/059678
§ 371 (c)(1),
(2), (4) Date: Nov. 19, 2013

(87) PCT Pub. No.: WO2012/163786
PCT Pub. Date: Dec. 6, 2012

(65) Prior Publication Data
US 2014/0107737 A1    Apr. 17, 2014

(30) Foreign Application Priority Data
May 27, 2011 (IE) .................................. S2011/0245

(51) Int. Cl.
*A61N 5/06* (2006.01)
*A61M 21/00* (2006.01)
(Continued)

(52) U.S. Cl.
CPC ............ *A61N 5/0618* (2013.01); *A01K 13/00* (2013.01); *A01K 13/006* (2013.01); *A61D 9/00* (2013.01);
(Continued)

(58) Field of Classification Search
CPC ...... A61N 5/06; A61N 5/0613; A61N 5/0618; A61N 5/0622; A61N 2005/0643; A61N 2005/0647; A61N 2005/0648; A61N 2005/0651; A61N 2005/0652; A61N 2005/0658; A61N 2005/0662;
(Continued)

(56) References Cited

U.S. PATENT DOCUMENTS 4,148,172 A    4/1979    Fer
4,858,609 A *  8/1989    Cole ..................... A61M 21/00
                                                            600/26
(Continued)

FOREIGN PATENT DOCUMENTS

GB        2335363 B        7/2002

OTHER PUBLICATIONS

Shabpareh, V. et al., 'An Alternative Artificial Lighting Regime to Hasten Onset of the Breeding Season in Mares,' Equine Practice, vol. 14, No. 2, Feb. 1992, pp. 24-27.*
(Continued)

*Primary Examiner* — Ahmed Farah
(74) *Attorney, Agent, or Firm* — Saul Ewing Arnstein & Lehr LLP (57) ABSTRACT

An apparatus for inhibiting melatonin synthesis in a horse comprises a blinker having an internal surface of which at least a part is diffusing. A source of light is positioned for direction into the horse's eye by the diffusing-surface. The light source and diffusing surface are configured such that the light directed into the horse's eye is blue.

21 Claims, 5 Drawing Sheets

(51) Int. Cl.
*B68B 1/10* (2006.01)
*A01K 13/00* (2006.01)
*A61D 9/00* (2006.01)
*A61D 99/00* (2006.01)

(52) U.S. Cl.
CPC .............. *A61D 99/00* (2013.01); *A61M 21/00* (2013.01); *B68B 1/10* (2013.01); *A61M 2021/0044* (2013.01); *A61M 2205/825* (2013.01); *A61M 2205/8206* (2013.01); *A61M 2250/00* (2013.01); *A61N 2005/0648* (2013.01); *A61N 2005/0651* (2013.01); *A61N 2005/0662* (2013.01); *A61N 2005/0666* (2013.01)

(58) Field of Classification Search
CPC .......... A61N 2005/0663; A61M 21/00; A61M 21/0005; A61M 21/0083
USPC ................................ 607/88–91, 93; 128/898
See application file for complete search history.

(56) References Cited

U.S. PATENT DOCUMENTS

| | | | |
|---|---|---|---|
| 5,599,274 A | 2/1997 | Widjaja et al. | |
| 6,459,919 B1* | 10/2002 | Lys | A61N 5/0616 315/291 |
| 6,528,954 B1* | 3/2003 | Lys | A61N 5/0616 315/158 |
| 8,003,130 B2* | 8/2011 | Gnann | A01K 29/00 424/535 |
| 8,303,635 B2* | 11/2012 | Hurst | A61M 21/00 128/898 |
| 8,992,589 B2* | 3/2015 | Olcese | A61N 5/06 514/12.1 |
| 2006/0207493 A1 | 9/2006 | Chasmar | |
| 2008/0170476 A1* | 7/2008 | Hurst | A61M 21/00 368/250 |

OTHER PUBLICATIONS

Author Unknown, "Research Archives—Equine Medical Research Database," Grayson-Jockey Club Research Foundation, Inc., Oct. 20, 2007, 18 pages, Retrieved from: web.archive.org/web/20071020150325/http://www.grayson-jockeyclub.org/archivesDisplay.asp?section=26.
Malinowski, K. et al., "Effects of Interrupted Photoperiods on the Induction of Ovulation in Anestrous Mares," Journal of Animal Science, vol. 62, No. 4, Oct. 1, 1985, pp. 951-955.
Murphy, Barbara et al., "Rapid Phase Adjustment of Melatonin and Core Body Temperature Rhythms Following a 6-H Advance of the Light/Dark Cycle in the Horse," Journal of Circadian Rhythms, BioMed Central, vol. 5, No. 1, Aug. 24, 2007, 9 pages.
Shabpareh, V. et al., "An Alternative Artificial Lighting Regime to Hasten Onset of the Breeding Season in Mares," Equine Practice, vol. 14, No. 2, Feb. 1992, pp. 24-27.
International Search Report for PCT/EP2012/059678, dated Sep. 11, 2012, 3 pages.
International Preliminary Report on Patentability for PCT/EP2012/059678, dated Nov. 27, 2013, 22 pages.
Brennan et al., "Light, dark, and melatonin: emerging evidence for the importance of melanin in ocular psychology," Eye, 21, 901-908 (2007).

* cited by examiner

APPARATUS AND METHOD FOR INHIBITING MELATONIN SYNTHESIS IN A HORSE

This application is a 35 USC 371 national phase filing of International Application PCT/EP2012/059678, filed May 24, 2012, which claims priority to Irish national application S2011/024, filed May 27, 2011, the disclosures of which are incorporated herein by reference in their entireties.

This invention relates to an apparatus and method for inhibiting melatonin synthesis in a horse especially, but not necessarily, for advancing the breeding season of non-pregnant mares.

BACKGROUND

Photoperiod signals are the primary regulators of reproduction in seasonally breeding animals. Melatonin is known as the hormone of darkness as its production by the pineal gland is confined to the night-time hours; thus it acts as a decoder of seasonal day length in seasonally breeding animals. Light inhibits melatonin synthesis. As days get longer in the spring, the duration of melatonin production is reduced and this lifts the inhibitory action of this hormone in a mare's reproductive activity. Horses, as long-day breeders, normally foal between May and October. However, the universal birthday for many horse breeds is January 1st. This necessitates a demand for early foals in order to produce mature yearlings and two year old racehorses to meet industry timelines for sales and racing schedules. Therefore advanced onset of the mare's breeding season is required.

Exposure of Thoroughbred breeding mares to lengthened hours of light beginning on December 1st and continuing for at least 8-10 weeks is standard industry practice in order to advance the reproductively active period of the mare's circa-annual reproductive cycle, thus permitting breeding from February 15th, the official start of the Thoroughbred breeding season. The maintenance of groups of mares indoors under lights during winter months is labour and energy intensive. Mares must remain indoors and require maintenance in terms of feeding, bedding and labour associated with their upkeep during this time. This comes at a high cost. The estimated upkeep for a mare during this time is £20/day (feed, bedding, labour, light) and if maintained for 10 weeks totals can involve costs of about £1400.

For this reason, pregnant mares are not usually maintained under lights to advance the perceived breeding season.

Multiple studies have investigated the influence of time of breeding on gestation length and found that the earlier in the year that the mare is bred, the longer the gestation period. Mares bred between January and May have on average a 10-day longer gestation period than mares bred during their natural breeding season. This has important implications for the industry as the mare has an approximate 11 month gestation period (~330 days). Provided that she foals on time, stud managers have one month to ensure she becomes pregnant again to prevent a later foaling date the subsequent year. If the gestation length of early foaling mares could be shortened it would provide crucial extra time to permit a successful timely conception for the subsequent pregnancy. A study (Hodge et al, 1982) has shown that the administration of artificial light to pregnant mares beginning December 1st significantly shortens the gestational length by 10 days. It is assumed that this is not commonly practiced in the industry due to the high cost associated with keeping all pregnant as well as non-pregnant mares under artificial lighting.

A more recent unpublished study has shown that not only is the gestational period lengthened in early foaling mares, but that the birth weight of foals born in January and February is significantly lower than for a foal born later in the year. The Hodge (1982) study showed a tendency towards higher birth weights in mares provided with artificial lighting. It is therefore desirable to reduce gestation length and increase foal birth weight in pregnant mares.

Currently, the only known solution is to leave the stable lighting on over housed mares. The literature (Palmer and Driancourt, 1981) states that a 100 Watt light bulb in a 12 ft×12 ft stall (enough light to read a newspaper) burning for 16 hrs a day provides sufficient light for this purpose. As stated, this is costly.

U.S. Pat. No. 4,858,609 discloses a bright light mask system for shining a high intensity light into a subject's eyes at pre-selected time periods to modify circadian rhythms. The system includes a mask adapted to be worn by the subject (possibly a race horse) for covering the subject's eyes regardless of body position. The mask includes at least one light admitting aperture that is transparent to light energy. A light source is coupled to the aperture for generating and directing light into the subject's eyes. At least 2000 lux of light having a wavelength in the range of 500 to 600 nanometers (nm) is delivered to each of the subject's eyes. A controller dictates the intensity of the light generated and the periods during which the light is on.

It is an object of the present invention to provide a more cost-effective apparatus and method for inhibiting melatonin synthesis in a horse.

SUMMARY OF THE INVENTION

According to the invention there is provided an apparatus for inhibiting melatonin synthesis in a horse, comprising a blinker having an internal surface of which at least a part is diffusing, and a source of light positioned for direction into the horse's eye via the diffusing surface, the light source and diffusing surface being configured such that the light directed into the horse's eye is blue.

It will be understood that the internal surface of the blinker is the surface of the blinker which in use faces the horse's eye and is usually, but not necessarily, concave or approximately concave.

In a preferred embodiment the light source emits blue light and the diffusing surface does not significantly filter the blue light.

Preferably the blue light has a peak wavelength of from 440 to 490 nm, preferably 459 to 484 nm, and most preferably 468 nm.

Preferably the light source has an intensity of from 10 to 100 lux, most preferably 10 to 50 lux.

The light source may comprise at least one LED.

Preferably the diffusing surface of the blinker is diffusively reflective.

Advantageously the light source is shielded to substantially avoid direct illumination of the horse's eye.

The blinker may be mounted in a mask adapted for fitting to a horse's head.

Preferably the mask contains only a single said blinker for directing blue light into only a single eye of the horse.

The apparatus preferably includes an automatic timer for turning the light source on and off at selected times.

The invention further provides a method of inhibiting melatonin synthesis in a horse, comprising directing diffused blue light into the horse's eye for at least one selected period of time.

Preferably the blue light is directed into only a single one of the horse's eyes at any given time.

The method may be used for the purpose of advancing the breeding season of non-pregnant mares, shortening the gestation length in early foaling mares, and/or increasing the birth weight of foals born in the early months of the year.

The method may also be used for the purpose of mitigating the effects of jet lag in a horse.

The invention is based upon the recognition that the photic pathways involved in circadian, neuroendocrine and neurobehavioural responses in the retina are independent of those that convert light signals to neural signals for the visual system. Melanopsin is the photopigment mediating these non-visual responses in conjunction with rod and cone cells and is found in a novel set of photoreceptors called intrinsically photosensitive retinal ganglion cells (ipRGCs). The action spectra for these photoreceptors show peak sensitivities in the short-wavelength region of the visible spectrum and studies conducted in mice and humans indicate a peak sensitivity range between 459 nm and 484 nm. Since, for horses, we are most interested in the circadian and neuroendocrine signals that reach the SCN (the part of the brain regulating biological rhythms), we chose a suitable wavelength range that has shown to be effective in other species and likely to be effective in horses, as we have shown. The light chosen is not light for vision, but light to stimulate the SCN.

The advantages of the invention are that mobile timed lighting can be provided to mares while they remain in their natural outdoor pasture environment. This means that the mares do not need to be housed indoors with the associated bedding, feed, electricity and labour costs. Not only will this facilitate an advanced reproductive breeding season for non-pregnant mares, but it will now permit highly cost effective means of reducing gestation length of pregnant mares and increasing foal birth weights.

BRIEF DESCRIPTION OF THE DRAWINGS

Embodiments of the invention will now be described, by way of example, with reference to the accompanying drawings, in which.

DESCRIPTION OF THE PREFERRED EMBODIMENT

Figure 1:
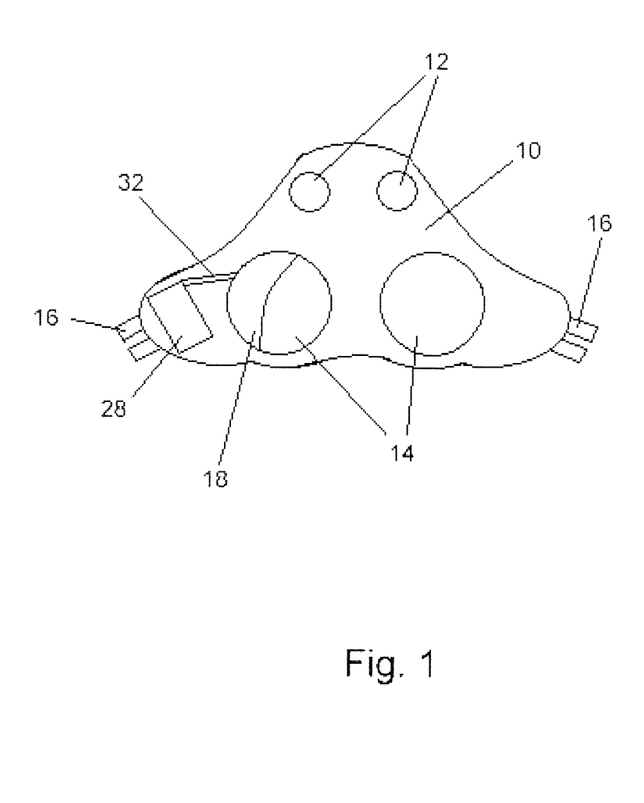
FIG. 1 is a schematic view of a mask for fitting to a horse's head, the mask incorporating a blinker according to a first illustrated embodiment of the present invention.

Referring to the drawings, a horse's face mask, FIG. 1, comprises a fabric base 10, approximately 600 mm wide, having ear openings 12, eye openings 14 and fasteners 16 for fastening the mask behind the horse's neck. To that extent the face mask is a conventional design.

Figure 2:
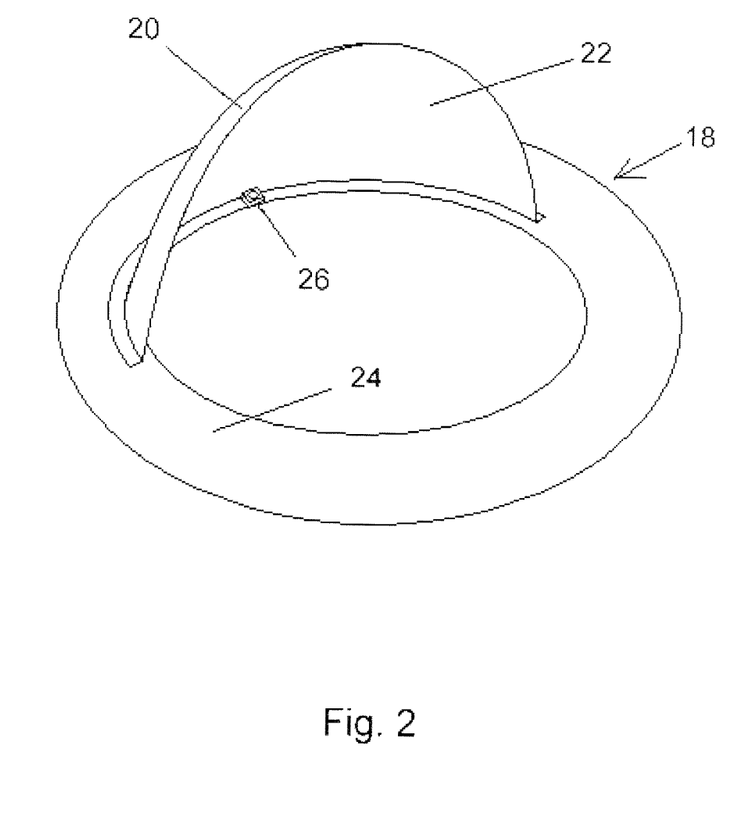
FIG. 2 is an enlarged view of the blinker in the mask of FIG. 1.

In accordance with a first illustrated embodiment of the invention, one of the eye openings 14 is fitted with a blinker 18, FIG. 2, the blinker comprising a rigid cup 20 having a diffusively reflective internal concave surface 22. The cup 20 is fixed to a semi-rigid annular base 24, the latter being fitted around the eye opening 14. The internal diameter of the annular base 24 is about 104 mm, and the height of the cup 20 is about 53 mm. An LED 26 emitting blue light is mounted on the blinker at the junction of the cup and base. The LED 26 is positioned to shine blue light on the reflective surface 22, from where it is diffused into the horse's cornea. The reflecting surface is white so that it does not significantly filter the blue light. The LED 26 is shielded from direct illumination of the horse's eye.

The construction of the mask such that the horse is exposed to diffuse light, that provides much less distraction than a light directly pointed at the eye. We have found that the behaviour of horses remained normal and they continued to feed or rest during the time they were exposed to the blue light.

The blinker 18 with blue LED 26 and reflecting surface 22 is fitted to only one of the two eye openings 14, since melatonin can be inhibited by administration of light to a single eye. This is important since the blue light administered to a single eye will not impede the natural behaviour of horses maintained outdoors at night, whereas light administered to both eyes might impede vision and movement. Horses that are blind in a single eye can move and behave normally. The other eye opening 14 would normally be left open, but if desired a conventional blinker could be fitted. It would also be possible to swap the LED blinker 18 from one eye opening 14 to the other at various times, to balance the effect on the horse, as long as the blue light is only administered to one eye at any given time.

Figure 3:
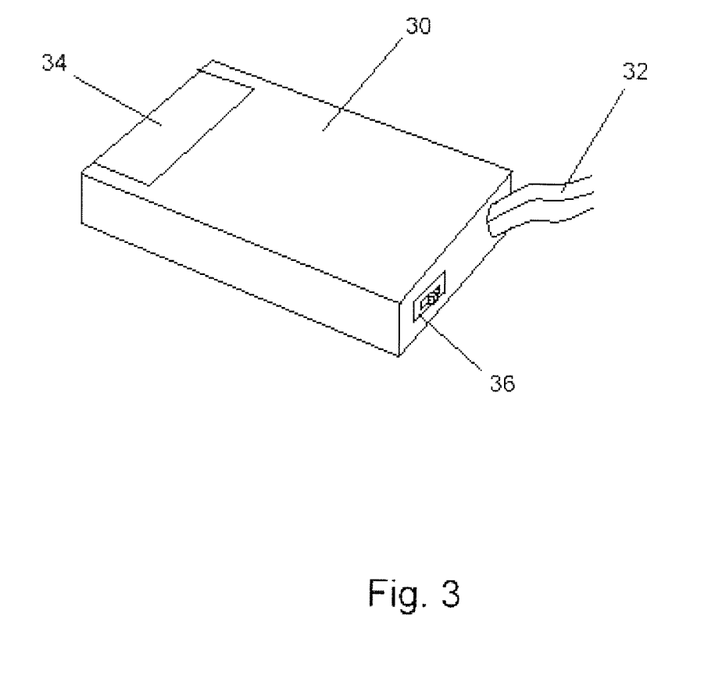
FIG. 3 shows a housing containing battery-powered circuitry for switching the LED on and off at selected times.

The fabric base 10 of the mask includes a pocket 28 for containing a power supply 30, FIG. 3, for the LED 26. The power supply is connected to the LED by leads 32 and has a battery compartment 34 for a replaceable and/or rechargeable battery, and an on/off switch 36. It is possible to operate the device manually, by switching the power supply on and off at various times, but it is preferred that the power supply include an automatic timer to turn the LED on and off at pre-selected times. Such a timer may be a manually settable timer or, more preferably, a programmable electronic circuit which can be programmed by computer, e.g. via a USB port. In this embodiment the power supply 30 has approximate dimensions 96 mm×60 mm×26 mm.

In variations of the first embodiment, diffuse light is directed towards the horse's eye without being reflected from a surface. In one example (not shown), an LED is provided with a diffusing lens surface and this is located towards the centre of the blinker and directed towards the horse's eye. The diffusing surface of the LED can be provided by for example, covering a lens surface in a generally transparent glue and curing the glue; and/or simply sanding the surface of the lens. This can diffuse light from the LED sufficiently not to be a distraction to the horse, but to nonetheless achieve the treatment goals outlined below.

Figure 4:
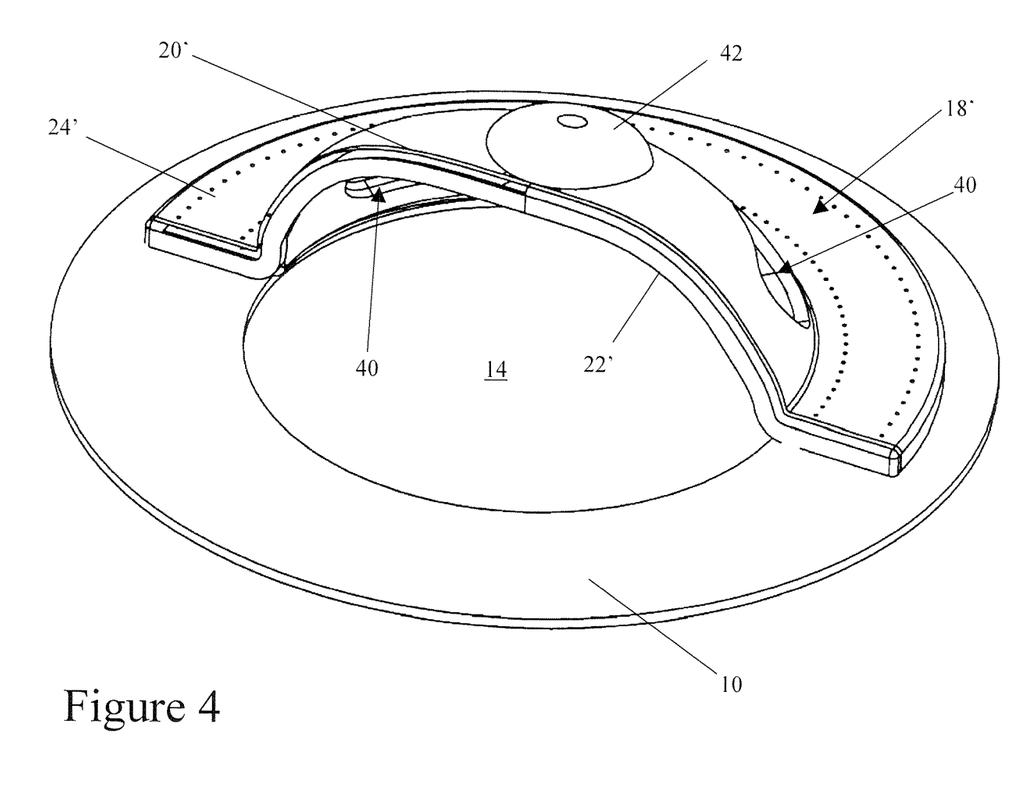
FIGS. 4 and 5 are perspective views of a blinker according to a second illustrated embodiment of the present invention.
Figure 5:
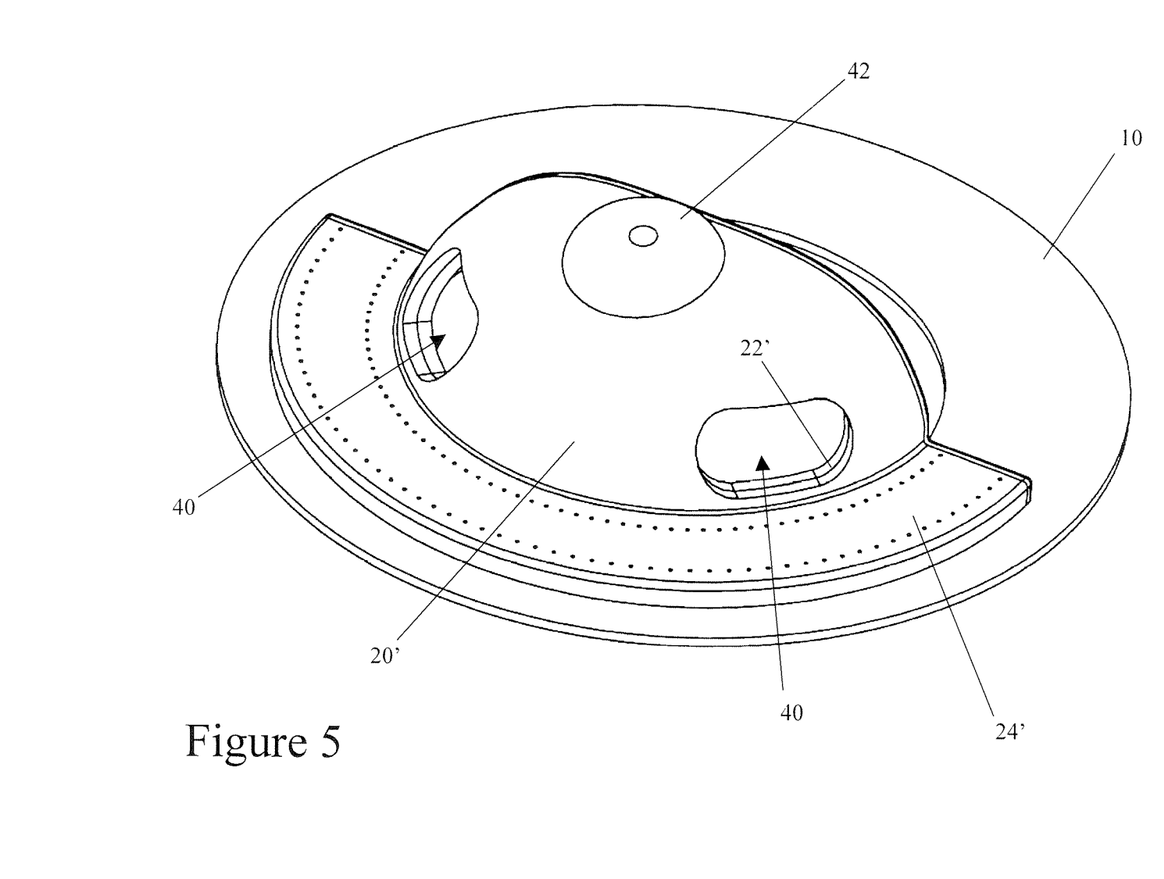

A second illustrated embodiment of the invention is shown in FIGS. 4 and 5. Here a blinker 18' again comprises a rigid or semi-rigid cup 20' of similar dimensions to the blinker 18 of the first embodiment. In this case, the cup 20' includes an integrally formed annular base 24', the latter being fitted around a harness eye opening 14. In this embodiment, a number of stitching holes 25 are defined in the base 24' and these can be used to sew the cup to the material of the harness, a portion 10 of which is shown.

A pair of windows 40 are defined in the cup 20' and it has been found that these can enable a horse to see through the blinker 18' without affecting the performance of the device. Similarly, one or more such windows could be defined in the blinker 18 of the first embodiment.

The internal surface of the cup 20' can be provided with a reflective and/or diffusing surface finish.

A recess 42 is defined at the centre of the cup 20' and is approximately 30 mm in diameter. A circular PCB (not shown) including a number, preferably 6, LEDS is located in the recess 42 with the LEDS being directed towards the opening 14. The LEDS are preferably disposed around the periphery of the PCB to provide a larger light emitting area than in the first embodiment and so make the blinker less susceptible to being blocked by dirt. The PCB is connected via wires (not shown) running from the recess externally of the blinker 18' to the power supply 30 shown in FIG. 3. The PCB can either include the necessary control electronics or the LEDs can be controlled from electronics located near the power supply.

In the second embodiment, an inner shell 22' is fitted within the cup 20'. The shell 22' is formed of a translucent diffusive material, for example, silicone. Thus, the shell 22' serves to retain the PCB in position; diffuse light emitted from the LEDs; and to seal the PCB from ingress of moisture.

In the present embodiments, the LED 26 emits blue light with a peak wavelength at 468 nm and we have found that 10-50 lux of such light directed at a single eye can inhibit the production of the hormone melatonin in the horse to daytime levels. This contrasts with natural daylight which provides anywhere from 1000 to 10,000 lux of light, depending on cloud cover. Using the embodiments, therefore, melatonin levels in the horse can be successfully inhibited using as little as 10-50 lux of blue light to a single eye.

We have found that the invention may be implemented using blue light in general, but preferably having a peak wavelength from 440 to 490 nm, and most preferably having a peak wavelength from 459 to 484 nm, as previously discussed. The lux levels of the blue light are very low compared to natural daylight, and preferably 10 to 100 lux and most preferably 10 to 50 lux. The blue light source may comprise more than one LED (or other lamp type) and if so the lux levels specified above refer to the combined output of all lamps.

The following regime of on/off blue light periods is recommended for advancing the breeding season of non-pregnant mares. The blue light is administered each day from about 1st December for at least 6 weeks, most preferably 6-8 weeks. The blue light is turned on before dusk and remains on so that the mare receives a combined total of at least about 16 hours of natural daylight and blue light each day (overlapping periods of daylight and blue light do not count double in the total).

Preliminary results have shown that use of the above described treatment regime can be at least as effective as maintaining animals indoors under barn lighting to advance the breeding season of mares.

In addition to advancing the breeding season of mares, the invention can be used to mitigate the effects of jet lag in a horse. Jet lag is considered one of society's most prevalent disorders and is a consequence of a misalignment of internal rhythms of physiology and a new light/dark cycle following abrupt changes in time zones (jet travel). Minimising disruption of circadian rhythms (24 h rhythms) is becoming an important area of research in order to minimise the risk of jet lag in athletes and thus sub-optimal performance (Reilly et al, 2005). We have shown in a recently published paper (Martin et al, 2010) that horses have circadian rhythms in activity and gene expression in skeletal muscle. In particular, key genes related to performance undergo a 24-h profile that is regulated by the light/dark cycle. Equine athletes are exposed to the same time zone displacements as their human counterparts due to the global nature of the industry and the ease of transporting these animals to international competition. Thus, jet lag is an issue for horses. Jet lag can be overcome if timed lighting that gradually adjusts to the light dark cycle at the destination is administered prior to travel. The present invention could facilitate this task without interrupting the management of the horses or their training regime.

The following regime of on/off blue light periods is recommended for mitigating the effects of jet lag on a horse: Dusk and dawn should be delayed or advanced, respectively, in selected daily increments (10 min, 30 min, 60 min) using light provided by the light mask, for a duration of time such that the animal is synchronized to the destination light/dark cycle prior to travel. Generally the light cycle should be advanced by a maximum of one hour per day when flying east and delayed by one hour per day when flying west. The number of days of light therapy should correspond roughly to the number of timezones crossed.

In the foregoing embodiments, the face mask is implemented as a full hood, but in the simplest case it could be configured as a simple mask just covering one eye.

In a variant of the first embodiment, the LED 26 could be a white light emitting LED, and the internal surface 22 of the cup 20 could be fabricated as a diffusively reflecting blue filter, either by providing a white diffusively reflecting surface with a separate transparent filter in front of it, or by making the internal surface itself of a blue diffusively reflecting material. In a similar variant of the second embodiment, the LEDs could also emit white light and the inner shell 22' of the cup 20' could act as a filter providing diffuse blue light.

Further variants of the above described embodiments, may include an automatic ambient light sensor that, in combination with the timer, can modulate the turn-on and/or turn-off times for maximum efficiency.

Equally, rather than simply switching the LEDs on and off at the beginning and end of illumination periods, illumination could be modulated in brightness so that for example, intensity could fade in and out over a period of 30 minutes.

Further variations of the above embodiments incorporate materials, which during or following illumination at certain wavelengths (or when heated or shaken) emit light at particular wavelengths.

Thus, the cup 20, 20' and/or shell 22' can be fabricated to include such a material, or mixture of materials, which emit visible light in the range to which the horse is sensitive as outlined above. Such materials, due to ambient conditions, emitting some constant or time varying amount of suitable light can supplement or replace the light from the LED light source, so cost effectively improving battery performance.

One mechanism for producing such light is photoluminescence. A material exhibiting photoluminescence soaks up energy from the environment (e.g. the light from the sun) and then slowly releases the energy stored over some specific range of wavelengths after dark.

Photoluminescence could be employed in embodiments of the invention in at least two ways:
 Doping the inner diffusing shell 22' with this material; or
 Covering the internal surface of the cup 20,20' and/or inner shell 22' with photo luminescent paint.

A suitable blue photo luminescent material, with a half-life of 3-6 hours i.e. the time it takes for the light emitted to drop to half its initial value would burn/emit light most brightly for a few hours after being illuminated by ambient light. Thus in a first phase of operation this material could provide the primary source of illumination. An ambient light sensor could then detect the level falling off, and then ramp up the LED source as appropriate. Again, the benefit of using these materials is that battery life would be prolonged, i.e., a smaller battery could be used, or more functions requiring electrical power incorporated in the device.

Indeed in further embodiments of the present invention, kinetically generated power can be harnessed from the horse's movement to power the light source and/or control electronics.

It is also observed that use of present invention advances the shedding of a horse's winter coat. This reduces the costs associated with either manually and/or accelerating shedding via housing under artificial light.

The invention is not limited to the embodiment(s) described herein but can be amended or modified without departing from the scope of the present invention.

The invention claimed is:

1. A light-based method of inducing physiological change, the method comprising the step of shining artificial blue light from an artificial blue light source, in which the artificial blue light source provides blue light with intensity of 100 lux or less, into just one eye of a horse or other animal, causing a suppression of melatonin production to induce physiological change, the physiological change being one of the group: advancing the breeding season of the horse or other animal; shortening the gestational length; increasing the birth weight; mitigating the effects of jet-lag; advancing the shedding of a winter coat, the method including the step of keeping the horse or other animal outdoors whilst the artificial blue light is shone in just one eye of the horse or other animal.

2. The method of claim 1 in which the light source provides only blue light with a peak wavelength in the range 440 nm-490 nm.

3. The method of claim 1 in which the light source provides only blue light with a peak wavelength in the range 459 nm-484 nm.

4. The method of claim 1 in which the light source provides blue light with intensity of under 100 lux.

5. The method of claim 4 in which the light source provides blue light with intensity of between 10-50 lux.

6. The method of claim 1 in which the light source is turned on before dusk.

7. The method of claim 1 comprising the step of keeping the horse or other animal in outside pasture for at least 6 weeks in the two or three months preceding the start of the horse or other animal's breeding season.

8. The method of claim 1 in which the animal is a horse.

9. The method of claim 1 in which the artificial light source is used from approximately 1 December for a period of approximately 6 weeks.

10. The method of claim 1 in which the artificial light source is a blue light LED.

11. The method of claim 1 in which the artificial blue light source includes a white light LED.

12. A light-based method of inducing physiological change, the method comprising the step of shining artificial blue light from an artificial blue light source, in which the artificial blue light source provides blue light with intensity of 100 lux or less, into just one eye of a horse or other animal, causing a suppression of melatonin production to induce physiological change, the physiological change being one of the group: advancing the breeding season of the horse or other animal; shortening the gestational length; increasing the birth weight; mitigating the effects of jet-lag; advancing the shedding of a winter coat, the method including the step of keeping the horse or other animal in outside pasture for at least 6 weeks in the two or three months preceding the start of the horse or other animal's breeding season.

13. The method of claim 12 in which the light source provides only blue light with a peak wavelength in the range 440 nm-490 nm.

14. The method of claim 12 in which the light source provides only blue light with a peak wavelength in the range 459 nm-484 nm.

15. The method of claim 12 in which the light source provides blue light with intensity of under 100 lux.

16. The method of claim 15 in which the light source provides blue light with intensity of between 10-50 lux.

17. The method of claim 12 in which the light source is turned on before dusk.

18. The method of claim 12 in which the animal is a horse.

19. The method of claim 12 in which the artificial light source is used from approximately 1 December for a period of approximately 6 weeks.

20. The method of claim 12 in which the artificial light source is a blue light LED.

21. The method of claim 12 in which the artificial blue light source includes a white light LED.

* * * * *